(12) United States Patent
Perez

(10) Patent No.: US 7,758,516 B2
(45) Date of Patent: Jul. 20, 2010

(54) METHOD AND APPARATUS FOR SAMPLING BODILY FLUID

(75) Inventor: Edward P. Perez, Redwood City, CA (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 1036 days.

(21) Appl. No.: 11/353,849

(22) Filed: Feb. 14, 2006

(65) Prior Publication Data
US 2007/0060845 A1 Mar. 15, 2007

Related U.S. Application Data

(62) Division of application No. 10/254,314, filed on Sep. 25, 2002, now abandoned.

(60) Provisional application No. 60/324,514, filed on Sep. 26, 2001.

(51) Int. Cl.
*A61B 5/00* (2006.01)
(52) U.S. Cl. .................................................. 600/583
(58) Field of Classification Search ................ 600/573, 600/583, 578, 584; 606/181, 182, 183
See application file for complete search history.

(56) References Cited

U.S. PATENT DOCUMENTS

| | | | |
|---|---|---|---|
| 2,646,799 A | 7/1953 | Jacoby | |
| 2,714,890 A | 8/1955 | Vang | |
| 3,030,959 A | 4/1962 | Grunert | |
| 3,086,288 A | 4/1963 | Balamuth et al. | |
| 3,208,452 A | 9/1965 | Stern | |
| 3,235,337 A | 2/1966 | Artis | |
| 3,623,475 A | 11/1971 | Sanz | |
| 3,626,929 A | 12/1971 | Sanz et al. | |
| 3,673,475 A | 6/1972 | Britton, Jr. | |
| 3,685,509 A | 8/1972 | Bentall | |
| 3,734,085 A | 5/1973 | Russell | |
| 3,741,197 A | 6/1973 | Sanz et al. | |

(Continued)

FOREIGN PATENT DOCUMENTS

DE 34 26 090 A1 4/1985

(Continued)

OTHER PUBLICATIONS

"Microlet Choice", Instructions on How to Use the Microlet Choice Low Pressure Sampling Blood Instrument, Japanese language document and English translation, Jun. 1997.
Ash et al., "Subcutaneous Capillary Filtrate Collector for Measurement of Blood Glucose", ASAIO Journal, 1992, vol./Issue No. 38 (3), pp. M416-M420, J.B. Lippincott Co.

(Continued)

*Primary Examiner*—Max Hindenburg
*Assistant Examiner*—Fangemonique Smith
(74) *Attorney, Agent, or Firm*—Woodard, Emhardt, Moriarty, McNett & Henry LLP

(57) ABSTRACT

Bodily fluid is sampled by causing a lancet mounted in a housing to be displaced toward a skin surface. A vacuum mechanism disposed on the housing is utilized to create a suction in the area to be incised causing bodily fluid to pool. The vacuum mechanism may then be deactivated thereby releasing the vacuum force on the skin, or repeatedly activated and deactivated. After the vacuum device has been utilized, the lancet is advanced to form an incision. The vacuum device may be activated, activated and deactivated, or repeatedly activated and deactivated after forming the incision. The sample may be withdrawn from the incision through a capillary tube.

17 Claims, 5 Drawing Sheets

U.S. PATENT DOCUMENTS

| | | |
|---|---|---|
| 3,832,776 A | 9/1974 | Sawyer |
| 4,077,406 A | 3/1978 | Sandhage et al. |
| 4,151,832 A | 5/1979 | Hamer |
| 4,154,228 A | 5/1979 | Feldstein et al. |
| D254,444 S | 3/1980 | Levine |
| 4,203,446 A | 5/1980 | Hofert et al. |
| 4,222,380 A | 9/1980 | Terayama |
| 4,223,674 A | 9/1980 | Fluent et al. |
| 4,356,826 A | 11/1982 | Kubota |
| 4,360,016 A | 11/1982 | Sarrine |
| 4,368,738 A | 1/1983 | Tersteegen et al. |
| 4,383,530 A | 5/1983 | Bruno |
| 4,441,510 A | 4/1984 | Worley et al. |
| 4,449,529 A | 5/1984 | Burns et al. |
| 4,462,405 A | 7/1984 | Erhlich |
| 4,503,856 A | 3/1985 | Cornell et al. |
| 4,517,978 A | 5/1985 | Levin et al. |
| 4,518,384 A | 5/1985 | Tarello et al. |
| 4,535,773 A | 8/1985 | Yoon |
| 4,553,541 A | 11/1985 | Burns |
| 4,577,630 A | 3/1986 | Nitzsche et al. |
| 4,580,564 A | 4/1986 | Anderson |
| 4,622,974 A | 11/1986 | Coleman et al. |
| 4,627,445 A | 12/1986 | Garcia et al. |
| 4,637,403 A | 1/1987 | Garcia et al. |
| 4,637,978 A | 1/1987 | Dappen |
| 4,648,408 A | 3/1987 | Hutcheson et al. |
| 4,653,511 A | 3/1987 | Goch et al. |
| 4,653,513 A | 3/1987 | Dombrowski |
| 4,658,821 A | 4/1987 | Chiodo et al. |
| 4,660,570 A | 4/1987 | Dombrowski |
| 4,685,463 A | 8/1987 | Williams |
| 4,750,489 A | 6/1988 | Berkman et al. |
| 4,787,398 A | 11/1988 | Garcia et al. |
| 4,790,979 A | 12/1988 | Terminiello et al. |
| 4,794,926 A | 1/1989 | Munsch et al. |
| 4,805,623 A | 2/1989 | Jobsis |
| 4,823,806 A | 4/1989 | Bajada |
| 4,844,095 A | 7/1989 | Chiodo et al. |
| 4,850,973 A | 7/1989 | Jordan et al. |
| 4,858,607 A | 8/1989 | Jordan et al. |
| 4,869,249 A | 9/1989 | Crossman et al. |
| 4,873,993 A | 10/1989 | Meserol et al. |
| 4,883,068 A | 11/1989 | Dechow |
| 4,895,147 A | 1/1990 | Bodicky et al. |
| 4,920,977 A | 5/1990 | Haynes |
| 4,924,879 A | 5/1990 | O'Brien |
| 4,953,552 A | 9/1990 | DeMarzo |
| 4,976,724 A | 12/1990 | Nieto et al. |
| 4,994,068 A | 2/1991 | Hufnagle |
| 4,994,073 A | 2/1991 | Green |
| 4,994,079 A | 2/1991 | Genese et al. |
| 4,995,402 A | 2/1991 | Smith et al. |
| 5,002,054 A | 3/1991 | Ash et al. |
| 5,014,718 A | 5/1991 | Mitchen |
| 5,029,583 A | 7/1991 | Meserol et al. |
| 5,035,704 A | 7/1991 | Lambert et al. |
| 5,047,044 A | 9/1991 | Smith et al. |
| 5,052,403 A | 10/1991 | Haber et al. |
| 5,054,499 A | 10/1991 | Swierczek |
| 5,066,859 A | 11/1991 | Karkar et al. |
| 5,070,884 A | 12/1991 | Columbus et al. |
| 5,070,886 A | 12/1991 | Mitchen et al. |
| 5,097,810 A | 3/1992 | Fishman et al. |
| 5,100,620 A | 3/1992 | Brenneman |
| 5,108,889 A | 4/1992 | Smith et al. |
| 5,145,565 A | 9/1992 | Kater et al. |
| 5,152,775 A | 10/1992 | Ruppert |
| 5,163,442 A | 11/1992 | Ono |
| 5,165,418 A | 11/1992 | Tankovich |
| 5,188,118 A | 2/1993 | Terwilliger |
| 5,189,751 A | 3/1993 | Giuliani et al. |
| 5,193,552 A | 3/1993 | Columbus et al. |
| 5,201,324 A | 4/1993 | Swierczek |
| 5,217,480 A | 6/1993 | Haber et al. |
| 5,222,504 A | 6/1993 | Solomon |
| 5,231,993 A | 8/1993 | Haber et al. |
| 5,271,385 A | 12/1993 | Bailey |
| 5,277,198 A | 1/1994 | Kanner et al. |
| 5,279,294 A | 1/1994 | Anderson et al. |
| 5,282,822 A | 2/1994 | Macors et al. |
| 5,318,583 A | 6/1994 | Rabenau et al. |
| 5,318,584 A | 6/1994 | Lange et al. |
| 5,320,607 A | 6/1994 | Ishibashi |
| 5,320,808 A | 6/1994 | Holen et al. |
| 5,353,806 A | 10/1994 | Heinzelman et al. |
| 5,366,470 A | 11/1994 | Ramel |
| 5,368,047 A | 11/1994 | Suzuki et al. |
| 5,387,203 A | 2/1995 | Goodrich |
| 5,395,387 A | 3/1995 | Burns |
| 5,402,798 A | 4/1995 | Swierczek et al. |
| 5,415,169 A | 5/1995 | Siczek et al. |
| 5,421,816 A | 6/1995 | Lipkovker |
| 5,445,611 A | 8/1995 | Eppstein et al. |
| 5,456,875 A | 10/1995 | Lambert |
| 5,458,140 A | 10/1995 | Eppstein et al. |
| 5,472,427 A | 12/1995 | Rammler |
| 5,474,084 A | 12/1995 | Cunniff |
| 5,487,748 A | 1/1996 | Marshall et al. |
| 5,514,152 A | 5/1996 | Smith |
| 5,518,006 A | 5/1996 | Mawhirt et al. |
| 5,529,074 A | 6/1996 | Greenfield |
| 5,545,174 A | 8/1996 | Schenk et al. |
| 5,554,166 A | 9/1996 | Lange et al. |
| 5,569,212 A | 10/1996 | Brown |
| 5,575,403 A | 11/1996 | Charlton et al. |
| 5,582,184 A | 12/1996 | Erickson et al. |
| 5,611,809 A | 3/1997 | Marshall et al. |
| 5,628,309 A | 5/1997 | Brown |
| 5,628,764 A | 5/1997 | Schraga |
| 5,630,986 A | 5/1997 | Charlton et al. |
| 5,632,410 A | 5/1997 | Moulton et al. |
| 5,638,828 A | 6/1997 | Lauks et al. |
| 5,662,127 A | 9/1997 | De Vaughn |
| 5,666,966 A | 9/1997 | Horie et al. |
| 5,671,753 A | 9/1997 | Pitesky |
| 5,680,872 A | 10/1997 | Sesekura et al. |
| 5,682,233 A | 10/1997 | Brinda |
| 5,700,695 A | 12/1997 | Yassinzadeh et al. |
| 5,707,384 A | 1/1998 | Kim |
| 5,709,699 A | 1/1998 | Warner |
| 5,714,390 A | 2/1998 | Hallowitz et al. |
| 5,720,924 A | 2/1998 | Eikmeier et al. |
| 5,730,753 A | 3/1998 | Morita |
| 5,738,244 A | 4/1998 | Charlton et al. |
| 5,746,217 A | 5/1998 | Erickson et al. |
| 5,758,643 A | 6/1998 | Wong et al. |
| 5,776,157 A | 7/1998 | Thorne et al. |
| 5,788,651 A | 8/1998 | Weilandt |
| 5,800,781 A | 9/1998 | Gavin et al. |
| 5,801,057 A | 9/1998 | Smart et al. |
| 5,810,199 A | 9/1998 | Charlton et al. |
| 5,823,973 A | 10/1998 | Racchini et al. |
| 5,830,219 A | 11/1998 | Bird et al. |
| 5,846,490 A | 12/1998 | Yokota et al. |
| 5,854,074 A | 12/1998 | Charlton et al. |
| 5,855,801 A | 1/1999 | Lin et al. |
| 5,857,983 A | 1/1999 | Douglas et al. |
| 5,863,800 A | 1/1999 | Eikmeier et al. |
| 5,871,494 A | 2/1999 | Simons et al. |
| 5,879,311 A | 3/1999 | Duchon et al. |
| 5,880,829 A | 3/1999 | Kauhaniemi et al. |
| 5,885,211 A | 3/1999 | Eppstein et al. |
| 5,885,219 A | 3/1999 | Nightengale |

| | | |
|---|---|---|
| 5,891,053 A | 4/1999 | Sesekura |
| 5,902,279 A | 5/1999 | Powles et al. |
| 5,916,222 A | 6/1999 | Iwasaki et al. |
| 5,916,229 A | 6/1999 | Evans |
| 5,935,864 A | 8/1999 | Schramm et al. |
| 5,938,679 A | 8/1999 | Freeman et al. |
| 5,947,957 A | 9/1999 | Morris |
| 5,948,695 A | 9/1999 | Douglas et al. |
| 5,951,492 A | 9/1999 | Douglas et al. |
| 5,951,582 A | 9/1999 | Thorne et al. |
| 5,968,063 A | 10/1999 | Chu et al. |
| 5,971,941 A | 10/1999 | Simons et al. |
| 5,997,561 A | 12/1999 | Bocker et al. |
| 6,015,392 A | 1/2000 | Douglas et al. |
| 6,027,459 A | 2/2000 | Shain et al. |
| 6,036,924 A | 3/2000 | Simons et al. |
| 6,048,352 A | 4/2000 | Douglas et al. |
| 6,056,701 A | 5/2000 | Duchon et al. |
| 6,071,249 A | 6/2000 | Cunningham et al. |
| 6,071,250 A | 6/2000 | Douglas et al. |
| 6,071,251 A | 6/2000 | Cunningham et al. |
| 6,071,294 A | 6/2000 | Simons et al. |
| 6,086,545 A | 7/2000 | Roe et al. |
| 6,093,156 A | 7/2000 | Cunningham et al. |
| 6,099,484 A | 8/2000 | Douglas et al. |
| 6,117,630 A | 9/2000 | Reber et al. |
| 6,120,462 A | 9/2000 | Hibner et al. |
| 6,132,449 A | 10/2000 | Lum et al. |
| 6,136,013 A | 10/2000 | Marshall et al. |
| 6,139,562 A | 10/2000 | Mauze et al. |
| 6,143,164 A | 11/2000 | Heller et al. |
| 6,146,361 A | 11/2000 | DiBiasi et al. |
| 6,152,942 A | 11/2000 | Brenneman et al. |
| 6,155,992 A | 12/2000 | Henning et al. |
| 6,156,051 A | 12/2000 | Schraga |
| 6,159,424 A | 12/2000 | Kauhaniemi et al. |
| 6,162,639 A | 12/2000 | Douglas |
| 6,171,325 B1 | 1/2001 | Mauze et al. |
| 6,176,865 B1 | 1/2001 | Mauze et al. |
| 6,183,489 B1 | 2/2001 | Douglas et al. |
| 6,193,673 B1 | 2/2001 | Viola et al. |
| 6,203,504 B1 | 3/2001 | Latterell et al. |
| 6,210,420 B1 | 4/2001 | Mauze et al. |
| 6,210,421 B1 | 4/2001 | Bocker et al. |
| 6,228,100 B1 | 5/2001 | Schraga |
| 6,231,531 B1 | 5/2001 | Lum et al. |
| 6,261,241 B1 | 7/2001 | Burbank et al. |
| 6,261,245 B1 | 7/2001 | Kawai et al. |
| 6,271,045 B1 | 8/2001 | Douglas et al. |
| 6,283,926 B1 | 9/2001 | Cunningham et al. |
| 6,285,454 B1 | 9/2001 | Douglas et al. |
| 6,306,104 B1 | 10/2001 | Cunningham et al. |
| 6,306,152 B1 * | 10/2001 | Verdonk et al. ............. 606/182 |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,352,514 B1 | 3/2002 | Douglas et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,455,324 B1 | 9/2002 | Douglas |
| 6,461,496 B1 | 10/2002 | Feldman et al. |
| 6,464,649 B1 | 10/2002 | Duchon et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,730,046 B1 | 5/2004 | Hamamoto et al. |
| 6,837,858 B2 * | 1/2005 | Cunningham et al. ....... 600/573 |
| 7,041,068 B2 | 5/2006 | Freeman et al. |
| 2001/0031931 A1 | 10/2001 | Cunningham et al. |
| 2002/0002344 A1 | 1/2002 | Douglas et al. |
| 2002/0004196 A1 | 1/2002 | Whitson |
| 2002/0052618 A1 | 5/2002 | Haar et al. |
| 2002/0082543 A1 | 6/2002 | Park et al. |
| 2002/0087110 A1 | 7/2002 | Effenhauser et al. |
| 2002/0103499 A1 | 8/2002 | Perez et al. |
| 2003/0199902 A1 | 10/2003 | Boecker et al. |

FOREIGN PATENT DOCUMENTS

| | | |
|---|---|---|
| DE | 35 08 365 A1 | 8/1985 |
| DE | 37 08 031 A1 | 11/1987 |
| EP | 0 212 906 A2 | 4/1987 |
| EP | 0 453 283 A1 | 10/1991 |
| EP | 0 568 024 A2 | 11/1993 |
| EP | 0 622 046 B1 | 2/1994 |
| EP | 0 671 146 A1 | 9/1995 |
| EP | 0 688 532 B1 | 12/1995 |
| EP | 1 112 717 A1 | 7/2001 |
| GB | 2 222 251 A1 | 2/1990 |
| JP | 08000598 A1 | 1/1996 |
| JP | 09-084781 | 3/1997 |
| WO | WO 85/04089 A1 | 9/1985 |
| WO | WO 88/00812 A1 | 2/1988 |
| WO | WO 95/10223 A2 | 4/1995 |
| WO | WO 96/37256 A1 | 11/1996 |
| WO | WO 97/08986 A1 | 3/1997 |
| WO | WO 97/42885 A1 | 11/1997 |
| WO | WO 97/43962 A1 | 11/1997 |
| WO | WO 9742888 A1 | 11/1997 |
| WO | WO 00/45708 A1 | 8/2000 |
| WO | WO 01/00090 A1 | 1/2001 |
| WO | WO 01/66010 A1 | 9/2001 |
| WO | WO 02/056769 A1 | 7/2002 |

OTHER PUBLICATIONS

Ash et al., "A Subcutaneous Capillary Filtrate Collector for Measurement of Blood Chemistries", ASAIO Journal, 1993, vol./Issue No. 39 (3), pp. M699-M705, J.B. Lippincott Co.

Brace et al., "Re-evaluation of the Needle Method for Measuring Interstitial Fluid Pressure", American Journal of Physiology, 1975, vol./Issue No. 229 (3), pp. 603-607, American Physiological Society.

Ginsberg, "An Overview of Minimally Invasive Technologie", Clinical Chemistry, 1992, vol./Issue No. 38 (9), pp. 1596-1600, Becton Dickinson and Co.

Janle-Swain et al., "Use of a Capillary Filtrate Collector for Monitoring Glucose in Diabetics", ASAIO Journal, 1987, pp. 336-340, J.B. Lippincott Co.

Kayashima et al., "Suction Effusion Fluid from Skin and Constituent Analysis: New Candidate for Interstitial Fluid", American Journal of Physiology, 1992, vol./Issue No. 263 (5), pp. H1623-H1627, American Physiological Society.

Korthuis, R.J. et al., "Interstitium & Lymphatic Techniques", Microcirculatory Technology, 1986, pp. 317-340, Academic Press, Inc.

Turner et al., "Diabetes Mellitus: Biosensors for Research and Management", Biosensors, 1985, vol./Issue No. 1 (1), pp. 85-115, Elsevier Applied Science Publishers, UK.

Wiig, Helge, Evaluation of Methodologies for Measurement of Interstitial Fluid Pressure (Pi): Physiological Implications of Recent Pi Data, Critical Reviews in Biomedical Engineering, 1990, vol./Issue No. 18-1, pp. 27-54, CRC Press, Boca Raton, Florida, US.

Abstract of JP 2000152923, Jun. 6, 2000, Terumo Corp.

Abstract of JP 2001095787, Apr. 10, 2001, Arkray Inc.

Abstract of JP 2170388, Jul. 2, 1990, Kyocera Corp.

Abstract of JP 6004150, Jan. 14, 1994, Casio Computer Co Ltd.

* cited by examiner

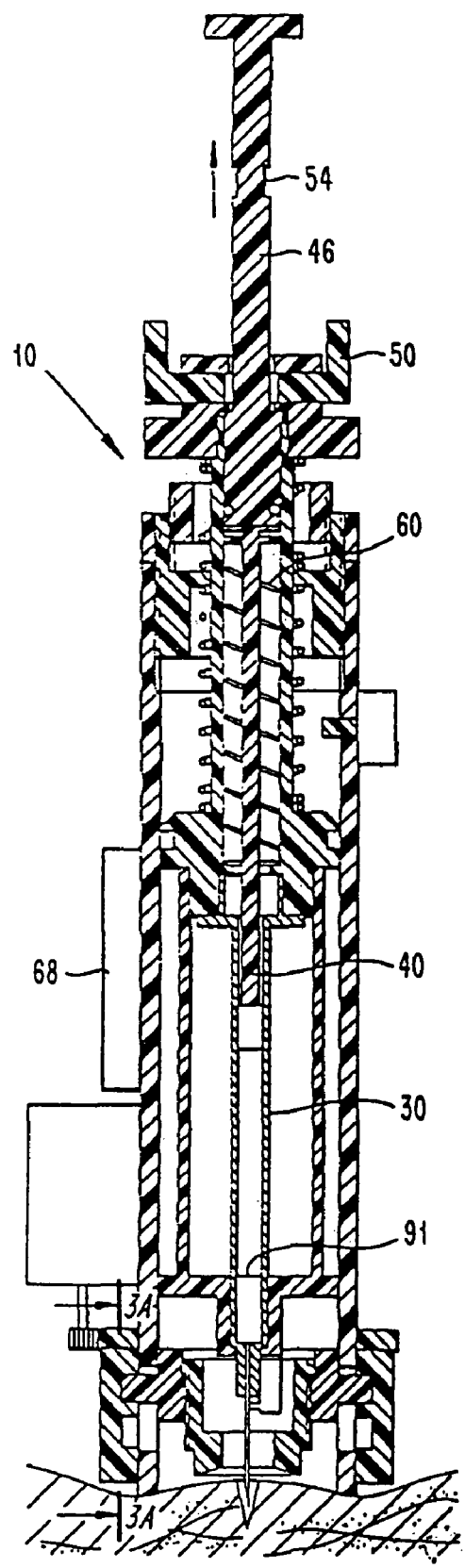
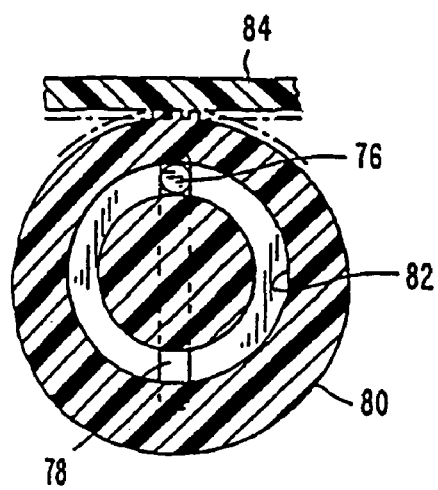
FIG. 3
FIG. 3A

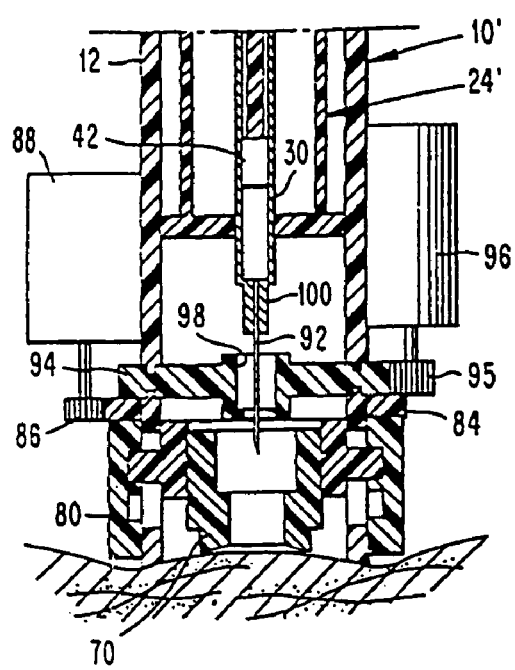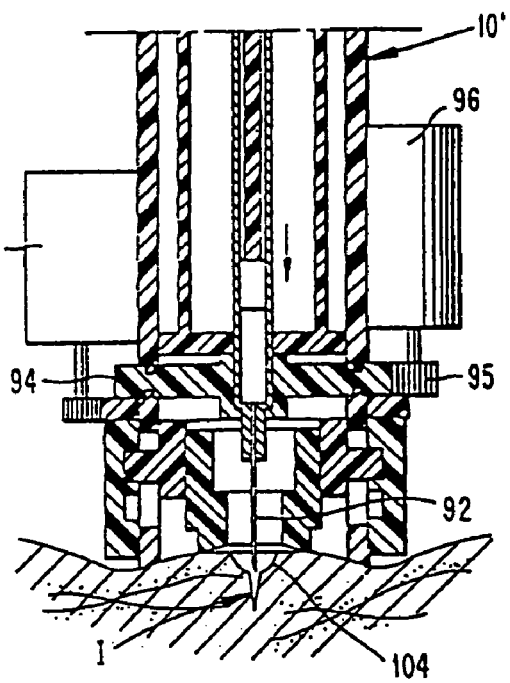
FIG. 8     FIG. 9
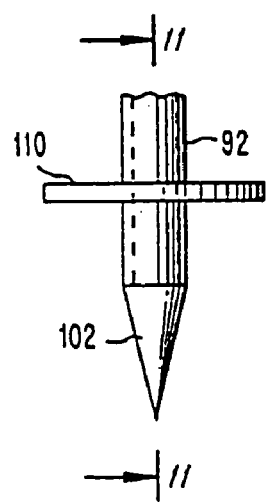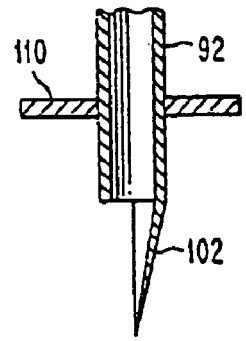
FIG. 10     FIG. 11

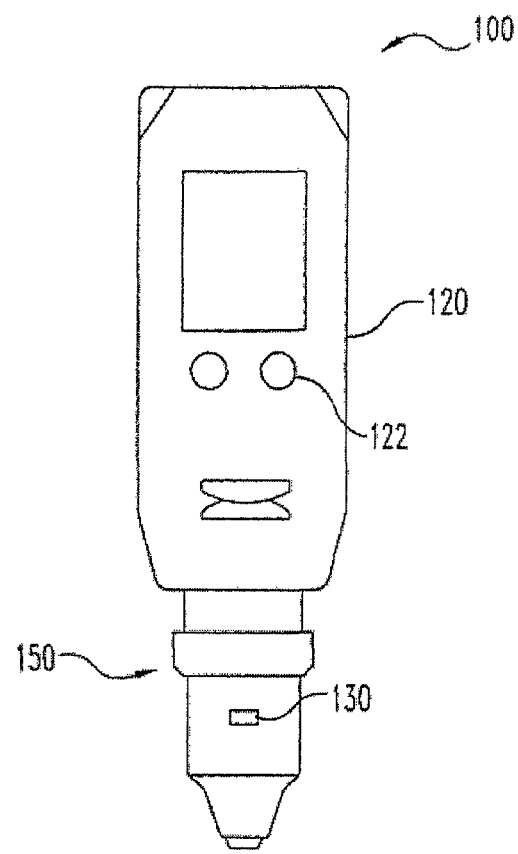
FIG. 12
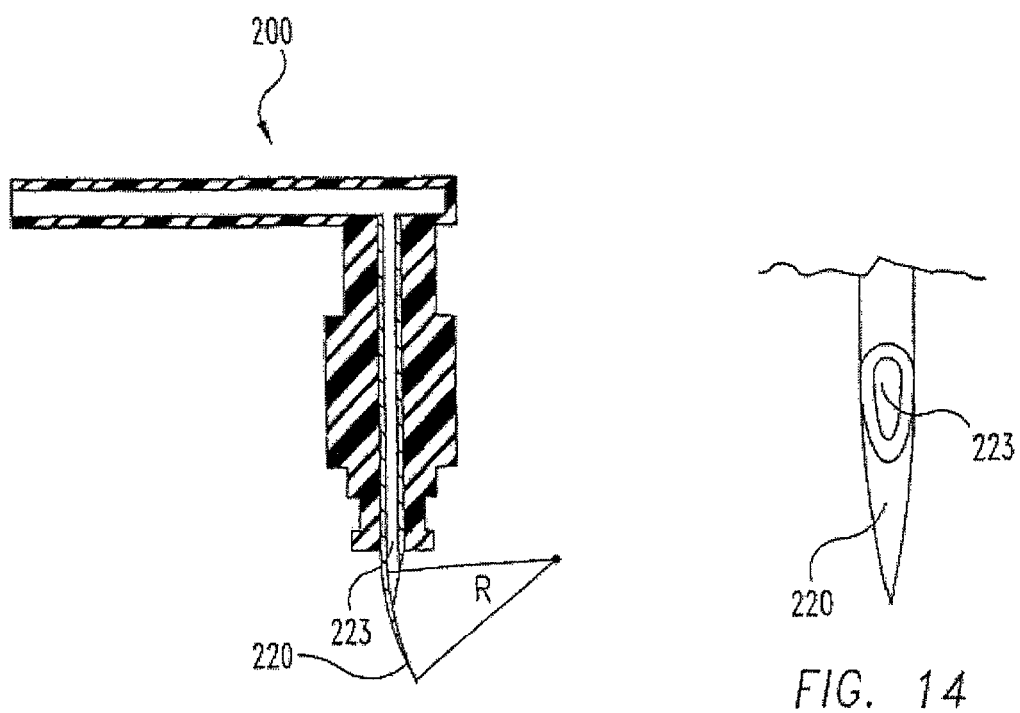
FIG. 13
FIG. 14

METHOD AND APPARATUS FOR SAMPLING BODILY FLUID

PRIOR APPLICATIONS

This application is a divisional of U.S. application Ser. No. 10/254,314, filed Sep. 25, 2002, which claims the benefit of U.S. Provisional Application No. 60/324,514, filed Sep. 26, 2001 the entireties of which are hereby incorporated herein by reference.

FIELD OF THE INVENTION

The present invention relates to lancing devices and methods for obtaining samples of blood and other fluids from a body for analysis or processing.

BACKGROUND OF THE INVENTION

Many medical procedures in use today require a relatively small sample of blood, in the range of 3-50 milliliters. It is more cost effective and less traumatic to the patient to obtain such a sample by lancing or piercing the skin at a selected location, such as the finger, to enable the collection of 1 or 2 drops of blood, than by using a phlebotomist to draw a tube of venous blood. With the advent of home use tests such as self monitoring of blood glucose, there is a requirement for a simple procedure which can be performed in any setting by a person needing to test.

Lancets in conventional use generally have a rigid body and a sterile needle which protrudes from one end. The lancet may be used to pierce the skin, thereby enabling the collection of a blood sample from the opening created. The blood is transferred to a test device or collection device. Blood is most commonly taken from the fingertips, where the supply is generally excellent. However, because the patient must perform multiple tests daily, the fingertips become sensitive or calloused thereby making it difficult to obtain a sample. Additionally, the nerve density in this region causes significant pain in many patients. Therefore alternate sampling sites, such as earlobes and limbs, is sometimes practiced to access a bodily fluid sample.

To reduce the anxiety of piercing the skin and the associated pain, many spring loaded devices have been developed. The following two patents are representative of the devices which were developed in the 1980's for use with home diagnostic test products.

U.S. Pat. No. 4,503,856, Cornell et al., describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

Levin et al. U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In institutional settings, it is often desirable to collect the sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

Haynes U.S. Pat. No. 4,920,977 describes a blood collection assembly with lancet and microcollection tube. This device incorporates a lancet and collection container in a single device. The lancing and collection are two separate activities, but the device is a convenient single disposable unit for situations when sample collection prior to use is desirable. Similar devices are disclosed in Sarrine U.S. Pat. No. 4,360,016, and O'Brien U.S. Pat. No. 4,924,879.

Jordan et al. U.S. Pat. No. 4,850,973 and U.S. Pat. No. 4,858,607, disclose a combination device which may be alternatively used as a syringe-type injection device and a lancing device with disposable solid needle lancet, depending on configuration.

Lange et al. U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

Suzuki et al. U.S. Pat. No. 5,368,047, Dombrowski U.S. Pat. No. 4,653,513 and Ishibashi et al. U.S. Pat. No. 5,320,607 each describe suction-type blood samplers. These devices develop suction between the lancing site and the end of the device when the lancet holding mechanism withdraws after piercing the skin. A flexible gasket around the end of the device helps seal the end around the puncture site until adequate sample is drawn from the puncture site or the user pulls back on the device.

Garcia et al. U.S. Pat. No. 4,637,403 and Haber et al. U.S. Pat. No. 5,217,480, disclose combination lancing and blood collection devices which use a diaphragm to create a vacuum over the wound site.

Erickson et al. U.S. Pat. No. 5,582,184 describes a means of collecting and measuring bodily fluids. This system uses a coaxial syringe and capillary tube disposed within a spacer member. The spacer member limits the depth of syringe penetration, and compresses body tissue around the syringe while the syringe is in the skin, for improving the flow of interstitial fluid to the syringe. A suction device draws bodily fluid through the syringe and into the capillary tube.

Single use devices have also been developed for single use tests, i.e. home cholesterol testing, and for institutional use to eliminate cross-patient contamination multi-patient use. Crossman et al. U.S. Pat. No. 4,869,249, and Swierczek U.S. Pat. No. 5,402,798, also disclose disposable, single use lancing devices. U.S. Pat. Nos. 5,421,816; 5,445,611; and 5,458,140 disclose, as a replacement for invasive sampling, the use of ultrasound to act as a pump for expressing interstitial fluid directly through intact (non-lanced) skin. The amount of fluid which can be obtained in that way is very limited, however.

The disclosures of the above patents are hereby incorporated herein by reference.

Even with the many improvements which have been made, the pain associated with lancing remains a significant issue for many patients. The need for blood sampling and the fear of the associated pain is also a major obstacle for the millions of diagnosed diabetics, who do not adequately monitor their blood glucose due to the pain involved. Moreover, lancing to obtain a blood sample for other diagnostic applications is becoming more commonplace, and a less painful, minimally invasive device is needed to enhance those applications and make those technologies more acceptable.

An object of the present invention therefore, is to provide a device and a method for obtaining a sample of bodily fluid through the skin which is virtually pain free and minimally invasive.

Therefore, it is another object of the invention to provide a lancet carrier which eliminates the above-mentioned shortcomings.

Another object of this invention is to provide a method which can result in a sample of either blood or interstitial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method which can draw a small but adjustable sample, i.e. 3 microliters for one test device and 8 microliters for another test device, as appropriate.

Another object of this invention is to provide a method by which the drawn sample is collected and may be easily presented to a testing device, regardless of the location of the sample site on the body. This approach helps with infection control in that multiple patients are not brought in contact with a single test instrument; only the sampling device with a disposable patient-contact portion is brought to the test instrument. Alternatively, the disposable portion of a test device may be physically coupled with the sampler so the sample can be brought directly into the test device during sampling. The test device may then be read in a test instrument if appropriate or the testing system can be integrated into the sampler and the test device can provide direct results displayed for the patient.

It is a further object of the invention is to provide a device for minimally invasive sampling comprising a reusable sampler and disposable sample collection.

Yet another object of the present invention is to provide a method of increasing the amount of bodily fluid available for sampling.

SUMMARY OF THE INVENTION

These and other objects are achieved by the present invention, one aspect of which relates to a method for sampling blood comprising the steps of placing a forward end of a housing against a skin surface, advancing a hollow piercing element forwardly to cut an incision through the skin surface, and depressing a ring of body tissue in surrounding relationship to the incision to spread apart sides of the incision while urging bodily fluid toward and into the incision. Simultaneously, the piercing element is moved within the incision to keep the incision open. A suction may be applied to the skin to aid the pooling of bodily fluid in the area of the incision. Additionally, a suction may be applied to the piercing element to draw in bodily fluid from the incision and into a tube communicating with the piercing element.

Another aspect of the present invention relates to a sampling device for sampling bodily fluid. The sampling device comprises a housing, a piercing element carrier mounted in the housing and carrying a hollow piercing element. A tube communicates with the piercing element. A driver mechanism mounted in the housing drives the syringe carrier forwardly to cut an incision in the skin and maintain and end of the piercing element in the incision. A stimulator mechanism disposed on the housing depresses a ring of body tissue in surrounding relationship to the incision to spread apart sides of the incision while urging bodily fluid toward the incision. A syringe-moving mechanism disposed on the housing moves the end of the piercing element relative to the incision to maintain the incision open while the stimulator mechanism urges bodily fluid thereto. A suction mechanism disposed on the housing creates a suction to cause bodily fluid to pool in the area to be incised, as will be described in greater detail below. Additionally, the suction element may be applied to the tube and utilized for drawing in bodily fluid through the piercing element and into the tube.

Still another aspect of the invention relates to a device for obtaining a sampling of a bodily fluid through the skin comprising a housing member containing a hollow piercing element for piercing the skin. A first spring member disposed in the housing urges the piercing element to protrude from a forward end of the housing sufficient to cut an incision through the skin. A stop member defines a maximum penetration depth of the piercing element. A second spring disposed in the housing partially retracts the piercing element while maintaining a front end of the piercing element in the incision. A tube communicates with a rear end of the piercing element. A suction mechanism creates a suction in the tube for drawing in bodily fluid through the piercing element.

BRIEF DESCRIPTION OF THE DRAWINGS

The objects and advantages of the invention will become apparent from the following detailed description of preferred embodiments thereof in connection with the accompanying drawings in which like numerals designate like elements and in which:

FIG. 3 is a view similar to FIG. 2 after a suction mechanism has been actuated to draw in bodily fluid through the syringe;

FIG. 3A is a sectional view taken along the line 3A-3A in FIG. 3;

FIG. 8 is a longitudinal sectional view of a lower portion of a modified sampling device according to the present invention, with a syringe disposed in a retracted state;

FIG. 9 is a view similar to FIG. 8 after the syringe has been urged forwardly;

FIG. 10 is a side elevational view of a lower end of a syringe having a stop member fixed thereto according to the present invention; and FIG. 11 is a sectional view taken along the line 11-11 in FIG. 10;

FIG. 12 is a top view of a integrated testing/lancing apparatus according to one embodiment of the present invention;

FIG. 13 is a cross-sectional side view illustrating an integrated lancet and test strip holder according to the present invention; and FIG. 14 is a side view illustrating the anti-coring needle in accordance with a lancing device of the present invention.

DESCRIPTION OF PREFERRED EMBODIMENTS

For the purposes of promoting an understanding of the principles of the invention, reference will now be made to the embodiments illustrated and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

Figure 1:
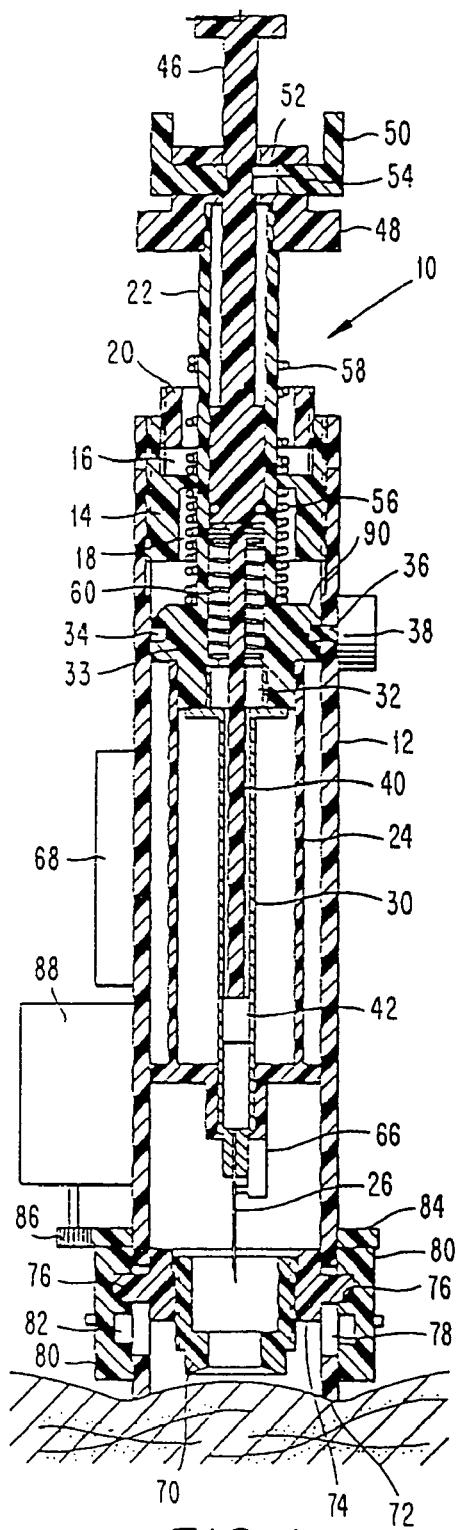
FIG. 1 is a longitudinal sectional view taken through a sampling device according to the present invention, with a syringe thereof in an armed state.
Figure 2:
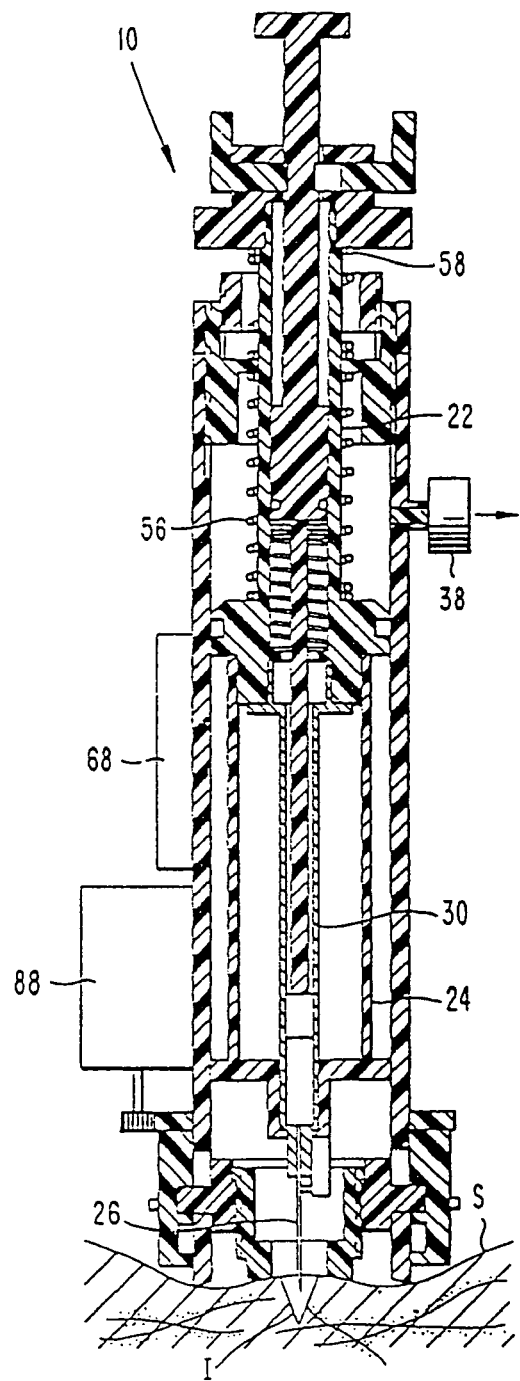
FIG. 2 is a view similar to FIG. 1 after the syringe has been triggered and forms an incision in a skin surface.

Depicted in FIGS. 1-3 is a bodily fluid sampling device 10 comprising an outer cylindrical housing 12. Screwed into an upper end of the housing 12 is a fixing sleeve 14 in which are formed upper and lower recesses 16, 18. The upper recess 16 has an internal screw thread connected to an externally threaded stop ring 20 which can be adjusted to a selected vertical position relative to the housing.

Figure 4:
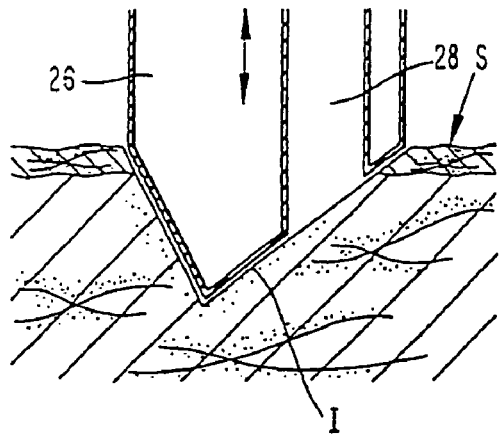
FIG. 4 is a schematic view of a syringe being reciprocated longitudinally within an incision according to the present invention.

Slidably disposed for longitudinal movement within the fixing sleeve 14 is a hollow drive rod 22. Screwed onto a lower end of the drive rod 22 is a syringe carrier 24. Mounted in a lower end of the carrier 24 is a syringe 26 of the type which includes a longitudinal capillary passage 28 (see FIG. 4). That passage is preferably offset laterally with respect to a center axis of the syringe. In lieu of a syringe, any suitable type of hollow piercing element can be employed, such as a needle or sharp cannula, for example. An upper end of the syringe communicates with a sampling tube 30, an upper end of the tube fitting into a lower recess 32 formed in the drive rod 22.

Intermediate its upper and lower ends, the drive rod 22 includes a radial enlargement 33 in which an outwardly open, annular groove 34 is formed that is sized to receive a pin 36 of a first trigger 38.

Slidably mounted within the sampling tube 30 is a plunger 40 having a soft tip 42 that snugly (sealingly) engages an inner surface of the tube 30. An upper end of the plunger 40 is fixed to the lower end of a drawbar 46 which slides within a center bore of the drive rod 22.

Screwed to an upper end of the drive rod 22 is a mounting sleeve 48 in which a second trigger 50 is mounted for lateral sliding movement. Formed in the second trigger 50 is a center hole 52 that is larger than the outer diameter of the drawbar 46. The drawbar 46 has a recess 54 sized to receive respective sides of the hole 52.

A drive spring 56 in the form of a coil compression spring acts between the enlargement 33 and the fixing sleeve 14. Resting on the fixing sleeve 14 is a retraction spring 58 in the form of a coil compression spring. Acting between the enlargement 33 and the top of the plunger 40 is a suction spring 60 in the form of a coil compression spring.

Mounted on the syringe carrier 24 is a piezoelectric transducer 66 which is electrically connected to a battery 68. Piezoelectric transducers are conventional types of vibrators which can be oriented to produce vibrations in any desired direction. A lower end of the piezoelectric transducer 66 is in contact with the syringe for vibrating the syringe, i.e., either vertically (longitudinally), laterally, or elliptically (a combination of vertical and lateral vibrations).

Disposed at a lower end of the housing 12 is a stimulator sleeve 70. That sleeve has an annular lower face of frusto-conical shape, and is screwed into a sleeve carrier 74. Projecting from diametrically opposite positions of the sleeve carrier 74 are pins 76 which are slidably disposed in respective vertical slots 78 formed in the housing 12.

Rotatably mounted on diametrically opposite sides of the housing 12 are a pair of identical drive gears 80 (see also FIG. 3A). Formed in an inner surface of each drive gear 80 is a cam groove 82 in which a respective pin 76 projects. Mounted above the drive gear for rotation about a central longitudinal axis of the housing is a ring gear 84 which is rotated by an output pinion 86 of an electric motor 88. The underside of the ring gear 84 is formed with teeth that mesh with teeth formed around the outer peripheries of the drive gears 80. Therefore, rotation of the pinion gear 86 is transmitted to the drive gears 80 to rotate the drive gears. The accompanying rotation of the eccentric grooves 82 of the drive gears causes the pins 76, and thus the sleeve carrier 74, to reciprocate vertically, along with the stimulator sleeve.

The operation of the sampling device 10 will now be explained. To arm the device, the mounting sleeve 48 is pulled upwardly by a user until a beveled face 90 of the enlargement 33 of the drive rod 22 cams the first trigger 38 laterally outwardly. When the groove 34 of the enlargement becomes aligned with the cammed-out first trigger 38, the first trigger is urged inwardly by a spring (not shown) to insert the pin 36 into the groove 34 for retaining the drive rod 22 in the armed state (FIG. 1). Simultaneously, the drive spring 56 is compressed from a relaxed state, and the syringe carrier 24, together with the syringe 26, is raised. The drawbar 46 is retained by the second trigger 50, with the suction spring 60 disposed in a compressed state.

The lower end 72 of the housing 12 is placed against the skin surface S, preferably at a portion of the body having fewer nerve endings than, say the fingertip. A forearm would be a suitable location. Suction may be applied to the skin surface S at this time. The suction may be applied and held, or applied and released prior to the syringe cutting the skin. The trigger 38 is then pulled out against a spring bias to release the drive rod 22 and the compressed drive spring 56. As a result, the drive rod 22, the syringe carrier 24, and syringe 26 are driven downwardly, so that the syringe cuts an incision I through the skin surface S, as shown in FIG. 2.

During downward movement of the drive rod 22, the mounting sleeve 48 engages an upper end of the retraction spring 58 and then abuts the stop ring 20, thereby limiting the incision depth and slightly compressing the retraction spring 58. The retraction spring 58 then moves the drive rod 22 slightly upwardly, but not enough to completely remove the syringe 26 from the incision I. Then, the motor 88 is actuated, either manually, or automatically in response to the firing of the syringe, to vertically reciprocate the stimulator sleeve 70. Consequently, the lower face of stimulator sleeve 70 repeatedly depresses a ring of skin and body tissue which surrounds the incision. Each depression of that ring causes the incision to bulge and the sides of the incision to be spread apart, and urges bodily fluid such as blood or interstitial fluid toward and outwardly through the incision I, as explained also in commonly assigned U.S. Pat. Nos. 5,879,311, and 5,591,493.

Figure 5:
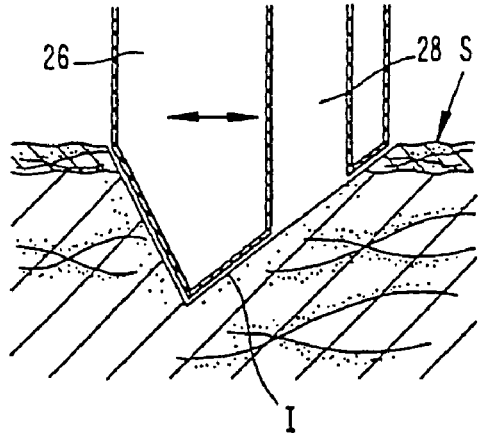
FIG. 5 is a schematic view of a syringe being reciprocated laterally within an incision according to the present invention.
Figure 6:
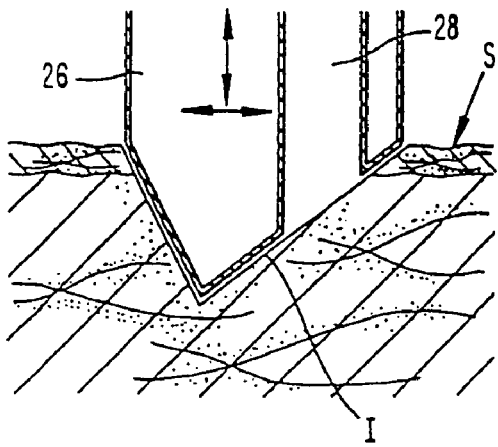
FIG. 6 is a schematic view of a syringe being oscillated in an elliptical direction according to the present invention.

In order to enable the inwardly urged bodily fluid to pool at the incision (for subsequent sampling), the syringe 26 is vibrated relatively slowly by the piezoelectric transducer 66 to keep the incision open. As noted earlier, the direction of vibration can be determined by the particular orientation of the transducer 66. In one embodiment, the direction of vibration is longitudinal or vertical (FIG. 4); in another embodiment the vibration is lateral (FIG. 5); in another embodiment the vibration is a combination of lateral and vertical, i.e., generally elliptical oscillation (FIG. 6).

It will be appreciated that if the syringe were not moved within the incision, the presence of a stationary syringe within the incision could result in a closing of the incision by collagen in the skin, whereby bodily fluid could not pool at the incision.

After a short period, sufficient to allow an ample amount of bodily fluid to pool at the incision, the second trigger 50 is manually actuated to release the drawbar 46, causing the spring 60 to raise the plunger 40 within the tube 30. That produces a suction in the tube 30 below the plunger 40, which draws in a sample 91 of bodily fluid through the syringe 26 (FIG. 3).

Then, the device can be removed from the skin, and the sample delivered to a suitable test site. Alternatively, the device may contain a test device in conjunction with the sampling device described above. Suitable test devices which may be incorporated with the sampler described above are shown and described in co-pending U.S. patent application Ser. No. 10/612,852, filed Jul. 3, 2003.

Figure 7:
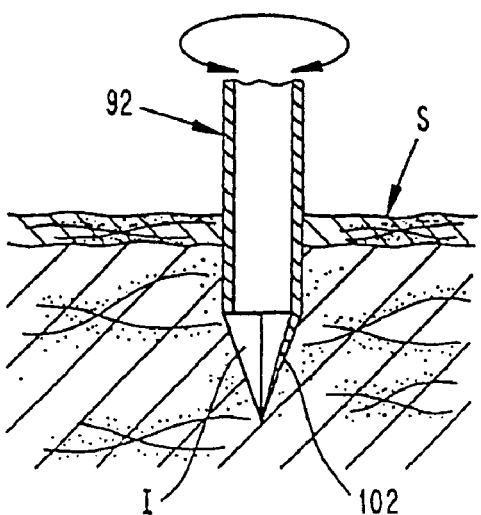
FIG. 7 is a schematic view of a syringe being rotated within an incision according to the present invention.

As an alternative to the reciprocation of the syringe, the syringe can be rotated about its own center axis while disposed in the incision I. In that regard, a rotatable syringe 92 as shown in FIG. 7 can be utilized in a device 10' shown in FIGS. 8 and 9. That device 10' is similar to that depicted in FIGS. 1-3 with the addition of a rotary gear 94 that is driven by a pinion 95 of a second motor 96. The gear 94 includes an upwardly open recess 98 sized to receive, with a snug fit, a lower end 100 of the tube 30 in which the syringe 92 is disposed. Thus, when the syringe carrier 24' is driven toward the skin, the lower portion 100 of the tube 30 enters the recess 98 to create a frictional engagement between the tube 30 and the gear 94 (see FIG. 9). By then rotating the pinion 95, the gear 94, the tube 30, and the syringe 92 are rotated relative to the carrier 24' about an axis coinciding with a center axis of the syringe 92. The syringe 92 includes a pointed end 102 in the form of one-half of a cone. As the syringe rotates about its own axis, the semi-conical segment 102 cuts a conical recess 104 in the incision and keeps the incision open as the stimulator sleeve 70 reciprocates.

Any of the syringes described thus far can be provided with a stop which would replace the stop ring 20. Such a stop 110 is shown in FIGS. 10 and 11 in connection with the syringe 92. The stop 110 comprises a disc fixed to the syringe. When the disc contacts the skin surface, no further entry of the syringe into the skin can occur. The stop ring 20 could also be used to open and close the incision to promote bodily fluid pooling.

It will be appreciated that the present invention minimizes the pain experienced by a user, because it can be used to provide a sample of bodily fluid at an area of the body which contains fewer nerve endings than in an area such as the finger tips. By stimulating the body tissue surrounding the incision, while moving the syringe relative to the incision, bodily fluid is caused to pool in the incision, thereby providing an ample sample to be sucked through the syringe and into a collection tube. Thus, an area of the body less sensitive to pain can be used as a source of bodily fluid.

Although the stimulator member 70 is disclosed as having a generally annular skin contacting surface, i.e., a surface which is symmetric about the center axis thereof, the member 70 could instead have an elliptical or polygonal end face whereby the ring of body tissue depressed thereby would have a corresponding shape.

An alternative method according to the present invention includes the use of a suction device prior to use of the lancing device. The lower end of the housing 12 is placed against the skin surface S, preferably at a portion of the body where the sample is to be taken from. For example, a forearm would be a suitable location. A vacuum source is activated whereupon the skin S adjacent the lower end of the housing 12 is drawn into the frusto-conical shaped distal tip. The suction causes bodily fluid beneath the skin to pool in the area of skin S in contact with the testing device 10. The vacuum is released thereby releasing the skin. The trigger 38 is then pulled out against a spring bias to release the drive rod 22 and the compressed drive spring 56. As a result, the drive rod 22, the syringe carrier 24, and syringe 26 are driven downwardly, so that the syringe cuts an incision I through the skin surface S. During the downward movement of the drive rod 22, the mounting sleeve 48 engages an upper end of the retraction spring 58 and then abuts the stop ring 20, thereby limiting the incision depth and slightly compressing the retraction spring 58. The retraction spring 58 then moves the drive rod 22 slightly upwardly, but not enough to completely remove the syringe 26 from the incision I. Then, the motor 88 is actuated, either manually, or automatically in response to the firing of the syringe, to vertically reciprocate the stimulator sleeve 70. Consequently, the lower face of simulator sleeve 70 repeatably depresses a ring of skin and body tissue which surrounds the incision. The depression of the ring causes the skin adjacent the incision to bulge and the sides of the incision spread apart, such that bodily fluid is urged from the incision in response to the applied force.

After a short period, sufficient to allow an ample amount of bodily fluid to pool at the incision, the second trigger 50 is manually actuate to release the drawbar 46, causing the spring 60 to raise the plunger 40 within the tube 30. This produces suction in the tube 30 below the plunger 40, which draws in a sample 91 of bodily fluid through the syringe. The sample may then be delivered to an appropriate test media or testing device as described above.

Additionally, as described above, the vacuum may be repeatedly applied to the skin prior to deployment of the needle to form the incision I. By repeatably applying a vacuum source to the skin S this encourages bodily fluid to pool in the location adjacent to where the incision is to be made. Because bodily fluid is pooled in this area prior to formation of the incision I, once the incision I is formed the sample of bodily fluid is easily collected because of the large volume of fluid available within the area.

It is further contemplated that the vacuum mechanism may be activated after the incision is formed to further express fluid from the incision. In addition to the vacuum source, it is also contemplated that a vibratory force, a heat force, and/or an ultrasonic force may be applied to the area to be lanced to further the expression of bodily fluid. Additionally, the vacuum may be repeatedly applied to the skin after the formation of incision I. Repeated application of a vacuum after the incision is formed encourages bodily fluid to continue to pool in the area adjacent to the incision, thereby aiding collection of the bodily fluid.

Referring now to FIG. 12 there is shown yet another alternative embodiment of the present invention. As shown in FIG. 12 the test device 100 comprises a main body 120, a test strip holder/tip assembly 130, and a lancing device 150. The functions of the testing device 100 are similar to that as described above with reference to testing device 10. The testing device 100 is prepared for use by first inserting a disposable lancet/test strip holder and test strip into the lancing device 150. The lancing device 150 is then prepared for use by pulling up on a driving mechanism (not shown) thereby compressing a driving spring (not shown). The device 100 is placed over an area to be lanced, wherein a vacuum mechanism disposed within the main body 120 and in communication with the tip assembly 130 is then activated (for example, by manipulation of control 122). Skin S is drawn into the distal end of the device 100. The vacuum mechanism may then be deactivated (for example, by further manipulation of control 122) thereby releasing the vacuum force on the skin, or repeatedly activated and deactivated.

After the vacuum device has been utilized, device 100 releases the driving spring, wherein a lancet is advanced through the patient's skin to form an incision I therein. The lancet may then be retracted from the incision I. Alternatively, it may be desirable to leave the lancet within or directly adjacent the incision for the reasons described above. Additionally, the vacuum device may be activated, activated and deactivated, or repeatedly activated and deactivated after forming the incision. Furthermore, a vibratory force may be applied to the lancet, the vibratory force may be applied vertically, horizontally, or any combination thereof.

A sample of bodily fluid may then be withdrawn from the incision and transported to a test area. The sample may be withdrawn from the incision through a capillary tube having one end disposed within the end of the test device 100 and the other end in communication with a chemical pad of a test strip and or electrochemical measuring device. Alternatively, the test strip may include capillary means such as a capillary tube or a cascading capillary. In yet another alternative embodiment, the test strip may be disposed adjacent to the distal end of the testing device wherein the lancet passes through an aperture in the test strip. The test strip may further include a gasket and/or a deep dermal constriction device. Furthermore, by placing the strip against the patient's skin and lancing there through this eliminates the need for a capillary to transport the bodily fluid from the incision to the test strip. This may lead to shorter sample times and/or lessen the likelihood of a failed test due to inadequate sample delivery.

In yet an additional alternative embodiment as shown in FIGS. 13 and 14, the test device 200 may include a test strip (not pictured) and lancet 220 which may be formed as an integrated unit. The lancet 220 may be embodied in the form of an anti-coring needle having a pre-bent radius of curvature R and a fluid inlet 223 such as that described in co-pending provisional patent application No. 60/297,098 filed on Jun. 8, 2001, the entirety of which is herein incorporated by reference. In this embodiment, the test device is placed over the area to be lanced, a vacuum is drawn on the skin thereby increasing the amount of bodily fluid adjacent the test device. The vacuum is release and the lancet is advanced thereby forming an incision within the patient's skin. Bodily fluid may then be withdrawn from the incision. The bodily fluid is then collected using one of the devices described above. After a sufficiently sized sample has been collected, the test device may be removed from the patient's skin, this may be prompted by a audible and/or visual marker. The test device will then deliver to the patient a visual indication of the test results.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of expressing bodily fluid from an incision in the skin, the method comprising:
    disposing a testing device against the skin at a bodily fluid sampling location, the testing device including a distal end portion forming a seal with the skin, a vacuum source communicating with the distal end portion of the testing device, and a lancing device;
    activating the vacuum source;
    creating a vacuum in the distal end portion of the testing device adjacent to the sampling location;
    drawing the skin into the distal end portion of the testing device and to a drawn-in position;
    deactivating the vacuum source after said activating;
    releasing the vacuum in the distal end portion of the testing device adjacent to the sampling location after said creating;
    releasing the skin from the drawn-in position in the distal end portion, said releasing the skin occurring after said drawing and in response to said releasing the vacuum;
    forming an incision in the skin with the lancing device, wherein said forming occurs after said activating, after said deactivating and after said releasing.

2. The method according to claim 1, further comprising reactivating the vacuum source after said forming an incision.

3. The method according to claim 2, further comprising additionally deactivating the vacuum source after said reactivating.

4. The method according to claim 1, further comprising collecting the bodily fluid for testing.

5. The method according to claim 4, wherein the testing device further includes a test strip, and wherein said collecting deposits bodily fluid onto the test strip.

6. The method according to claim 5, wherein the test strip is electrochemical.

7. The method according to claim 5, further comprising determining the level of glucose in the bodily fluid, and displaying the level on a display included on the testing device.

8. The method according to claim 1, wherein the testing device further includes a stimulating device disposed about the distal end portion of the testing device, the method further comprising stimulating the area of the skin to be lanced with the stimulating device to pucker the skin.

9. The method according to claim 1, wherein the lancing device is solid and contains no holes.

10. The method according to claim 1, further comprising maintaining the testing device against the skin at the bodily fluid sampling location during said activating, said creating, said drawing, said deactivating, said releasing the vacuum, said releasing the skin and said forming.

11. A method of obtaining a sample of capillary whole blood from a target tissue, comprising:
    providing a penetrating system that includes a tissue stabilizing member, a tissue stimulation member, and a vacuum source;
    drawing the target tissue into the tissue stabilizing member and to a drawn-in position with the vacuum source;
    releasing the vacuum source after said drawing;
    releasing the target tissue from the drawn-in position within the tissue stabilizing member, said releasing the target tissue occurring after said releasing the vacuum and in response to said releasing the vacuum;
    applying skin stimulation to the target tissue with the tissue stabilizing member;
    introducing a penetrating member through the target tissue to form an incision after said releasing the target tissue; and
    collecting blood from the incision in the penetrating system.

12. The method of claim 11, wherein the skin stimulation is a vibratory motion applied to the target tissue.

13. The method of claim 11, wherein the skin stimulation increases blood circulation at the target tissue.

14. The method of claim 11, wherein the skin stimulation is a heat force applied to the target tissue.

15. The method according to claim 8, wherein the stimulating includes applying a vibratory force to the target tissue.

16. The method according to claim 15, wherein the stimulating includes applying an ultrasonic vibratory force to the target tissue.

17. The method according to claim 1, further comprising applying a heat force to the bodily fluid sampling location with the testing device.

* * * * *